United States Patent
Grant et al.

(10) Patent No.: US 6,947,126 B2
(45) Date of Patent: Sep. 20, 2005

(54) DILUTION APPARATUS AND METHOD OF DILUTING A LIQUID SAMPLE

(75) Inventors: Donald C. Grant, Excelsior, MN (US); Mark R. Litchy, Plymouth, MN (US); Mary Kristin Nicholes, Eden Prairie, MN (US)

(73) Assignee: The BOC Group, Inc., Murray Hill, NJ (US)

(*) Notice: Subject to any disclaimer, the term of this patent is extended or adjusted under 35 U.S.C. 154(b) by 103 days.

(21) Appl. No.: 10/322,238

(22) Filed: Dec. 18, 2002

(65) Prior Publication Data
US 2003/0174306 A1 Sep. 18, 2003

Related U.S. Application Data
(60) Provisional application No. 60/363,933, filed on Mar. 13, 2002.

(51) Int. Cl.[7] .................................................. G01N 1/00
(52) U.S. Cl. ....................................................... 356/36
(58) Field of Search ........................... 356/36, 335–343; 250/576

(56) References Cited

U.S. PATENT DOCUMENTS

| | | | | |
|---|---|---|---|---|
| 4,333,735 A | * | 6/1982 | Hardy et al. ................. | 436/114 |
| 5,007,297 A | * | 4/1991 | Sommer ..................... | 73/865.5 |
| 5,191,388 A | * | 3/1993 | Kilham ....................... | 356/335 |
| 5,668,330 A | * | 9/1997 | Bartlett-Hooker et al. ............ | 73/864.81 |
| 6,211,956 B1 | * | 4/2001 | Nicoli ......................... | 356/337 |
| 6,380,454 B1 | * | 4/2002 | Gonzalez et al. ............ | 588/207 |
| 6,387,328 B1 | * | 5/2002 | Berndtsson ................... | 422/73 |
| 6,418,802 B1 | * | 7/2002 | Wood ......................... | 73/865.5 |
| 2003/0063271 A1 | * | 4/2003 | Nicholes et al. .............. | 356/36 |
| 2003/0076495 A1 | * | 4/2003 | Nicholes et al. ............. | 356/338 |
| 2003/0174306 A1 | * | 9/2003 | Grant et al. .................. | 356/36 |

* cited by examiner

*Primary Examiner*—Michael P. Stafira
(74) *Attorney, Agent, or Firm*—David A. Hey (57) ABSTRACT

A dilution apparatus for continuously producing a diluted liquid sample, e.g., a chemical-mechanical polishing slurry, for analysis, e.g., particle size distribution, comprises a mixer manifold, a diluent-introducing means, e.g., a flow controlling device, for introducing a diluent, e.g., water, into the mixer manifold, and a liquid sample introducing means, e.g., a pump, for introducing the sample into the mixer manifold. The mixer manifold includes a plurality of ports for receiving a plurality of liquid samples from a plurality of sample points. The dilution apparatus can include a second mixer manifold for continuously producing a second diluted liquid sample, and it can be associated with one or more sensors operable to measure sample properties, e.g., an optical particle counter. The sensors can be operated simultaneously, and the measurements of the sensors can be compared. The dilution apparatus is capable of improving accuracy, reliability, repeatability, sensitivity and versatility of the associated sensors, and it is less complex than conventional dilution systems.

30 Claims, 5 Drawing Sheets

FIG. 1A

| STEP | PRIMARY FUNCTION | MINOR FUNCTION | ACTIVATED VALVES | TIME(S) | SYRINGE? | FLOW CONTROLLER |
|---|---|---|---|---|---|---|
| 1 | LOADING SAMPLE LOOP | TIMER | 15 | 30 | NO | YES |
| 1 | START MEASUREMENT | VESSEL FLUSHING | 11, 12, THEN 11 OFF AND 14 | 30 | NO | YES |
| 2 | START MEASUREMENT | CHECKING BACKGROUND | 11, 14 THEN 12 AND 13 | 25 | YES, INITIALIZES | YES |
| 3 | START AUTODILUTION | (0) WAITING | 12, 13 THEN 11, 13 | 10 | YES | YES |
| 4 | START AUTODILUTION | (1) WAITING | 11, 13 | 40 | YES | YES |
| 5 | START AUTODILUTION | (2) WAITING | 11, 13 | 0.5 | NO | NO |
| 6 | MEASURING | TIMER | 11, 13 | 60 | YES | YES |
| 7 | STOP COLLECTING DATA | WAITING DATA | NONE | 0.5 | NO | NO |
| 8 | VESSEL FLUSHING | TIMER | 11, 12 THEN 12, 13, 14 | 90 | NO | YES |
| 9 | VESSEL FLUSHING | TIMER | 12, 14 | 90 | NO | YES |
| 10 | CHECKING BACKGROUND | TIMER | 11, 14 | 25 | NO | YES |

DILUTION APPARATUS AND METHOD OF DILUTING A LIQUID SAMPLE

CROSS-REFERENCE TO RELATED APPLICATIONS

Priority is claimed to U.S. provisional patent application Ser. No. 60/363,933 filed on Mar. 13, 2002.

BACKGROUND OF THE INVENTION

The invention relates to the preparation of liquid samples for analysis. In one aspect, the invention relates to a method for diluting the samples while in another aspect, the invention relates to an apparatus in which the samples are diluted. In yet another aspect, the invention relates to the sampling of a chemical-mechanical polishing slurry for the purpose of monitoring one or more properties of the slurry.

Liquids are used in many processes and applications. Often the composition of the liquid is important to the efficacy of the process or application, and often the composition of the liquid will change with use and/or time. Accordingly, such liquids are often monitored to ensure that their compositions remain within prescribed specifications.

One common form of monitoring a liquid used in a process involves obtaining a sample of the liquid and performing an off-line analysis upon it. Depending upon the process, the monitoring may require obtaining a plurality of samples either at one time or over a period of time. Depending upon the nature of the liquid and the analysis, and perhaps other factors as well, the liquid sample may or may not require some form of preparation before analysis. One form of preparation is dilution of the liquid sample.

By way of an example of a liquid that is used in a process and that requires frequent monitoring of its composition, chemical-mechanical polishing (CMP) systems are often employed in the microelectronics industry to planarize and/or polish semiconductor wafers. These systems typically contain and employ a "slurry" which is circulated throughout the system such that the slurry contacts and/or impinges upon the wafers. As the slurry impacts and/or passes over the wafers, the wafers are planarized and polished. One example of a slurry typically used in CMP systems is Semi-Sperse® 12 (SS-12) manufactured by Cabot Corporation of Aurora, Ill.

In order to maintain the consistency, performance, efficiency, and/or usefulness of the system, the "health" of the slurry must be maintained. Slurry instability, external contamination and/or process conditions (e.g., shear-inducing pressure gradients, flow rates, and exposure to air) may compromise slurry health. Thus, slurry properties (e.g., specific gravity, pH, weight percent solids, ionic contamination level, zeta potential, particle size distribution, etc.) are often closely monitored by a sampling system.

One such system for monitoring a CMP slurry is the intelligent Slurry Particle Equipment (iSPEQ) system which is described in commonly-owned, co-pending U.S. Ser. No. 60/313,440 filed Aug. 17, 2001 and entitled "Sampling and Measurement System with Multiple Slurry Chemical Manifold". The iSPEQ typically comprises an AccuSizer 780/OL (manufactured by Particle Sizing Systems of Santa Barbara, Calif.), a multi-port valve manifold, a sample station, one or more system drains and an aspirator. The iSPEQ system uses a unique method for flushing its multi-port manifold. This method is described in commonly-owned, co-pending U.S. Ser. No. 60/313,439 filed Aug. 17, 2001 and entitled "Flushing a Multi-Port Valve Manifold". In addition, the iSPEQ uses another method for collecting slurry from the sample station using the aspirator and multi-port manifold. This method is described in commonly-owned, co-pending U.S. Ser. No. 60/313,442 filed Aug. 17, 2001 and entitled "Chemical-Mechanical Polishing Sampling System Having Aspirator Drawn Pneumatics."

The iSPEQ was primarily designed to measure the particle size distribution (PSD) of CMP slurries. Of all the slurry health parameters, perhaps the most important and frequently measured is the PSD of the bulk or "working" particles and the "large particle tail" of the PSD. Particle size distribution may be graphically represented by the concentration of particles as a function of particle diameter. In slurries such as SS-12, the PSD of the working particles is sufficiently approximated by a Gaussian Distribution where the peak or highest concentration of particles is centered between particles that are roughly 0.05 to 0.5 $\mu$m in diameter. Slurries typically contain extremely high concentrations of particles less than 0.5 $\mu$m in diameter. The region of the PSD that illustrates the concentration of particles for diameters greater than 0.5 $\mu$m is commonly referred to as the "large particle tail" of the PSD.

In the industry, the large particle tail can be measured using a variety of techniques (e.g. light scattering, light extinction, etc.) and instruments such as sensors, analyzers, and like devices (collectively referred to as sensors), that are commercially available from a host of manufacturers. Many different measurement devices have been tested, compared, and evaluated for their ability to measure PSDs, and optical particle counting is widely accepted as the most sensitive type of measurement technique.

In general, sensors based upon optical particle counting (these sensors are referred to as "optical particle counters" or "OPCs") are used to measure the large particle tail of a slurry (those particles larger than about 0.5 $\mu$m in diameter). Optical particle counters count individual particles within a diluted slurry (e.g., silica, contaminants, debris, impurities, and the like) as the particles pass through a light beam. The slurry must be diluted enough so that only one detectable particle passes through the light beam at a time.

To produce a "diluted slurry" or "diluted liquid sample", a diluent and a slurry are blended and/or mixed together. The diluent can include various grades of water, e.g., deionized, demineralized, ultra-pure, etc., as well as other liquids, e.g., water with a pH adjusted to that of the slurry sample, an organic solvent, etc. Depending upon a variety of factors, e.g., the nature of the slurry, the capabilities of the sensor, etc., proper dilution of the slurry sample for analysis may require several steps, i.e., the slurry sample is diluted to create a first diluted slurry, and then the first diluted slurry is itself diluted to create a second or further diluted slurry. This process can repeat itself as many times as necessary so as to achieve the desired diluted slurry for analysis.

To repeatedly generate a diluted slurry having an optimum "dilution ratio" (i.e., the ratio of the diluent volume to the slurry sample volume), some OPCs are integrated into an automatic dilution system. An example of a device that contains both a sensor and an "auto-dilution" system is the AccuSizer 780/OL (AccuSizer system). The AccuSizer system, as well as its auto-dilution apparatus, are described in detail in U.S. Pat. No. 4,794,806 (Nicoli, et. al.) and U.S. Pat. No. 5,835,211 (Wells, et. al.). Throughout this disclosure "AccuSizer system" refers to the combination of the auto-dilution apparatus and the sensor, and "AccuSizer sensor" refers to just the sensor component in the AccuSizer system.

Figure 1A:
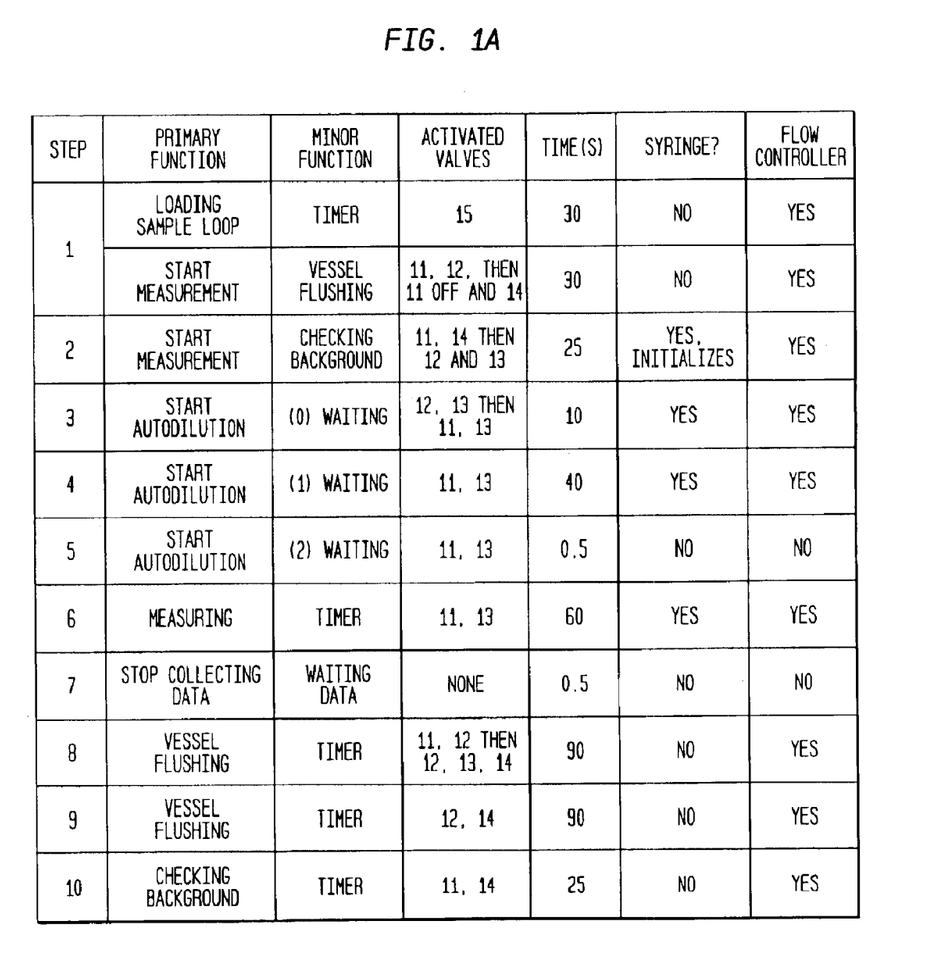
FIG. 1A is a table describing the ten operational steps of the AccuSizer system's auto-dilution apparatus.
Figure 1B:
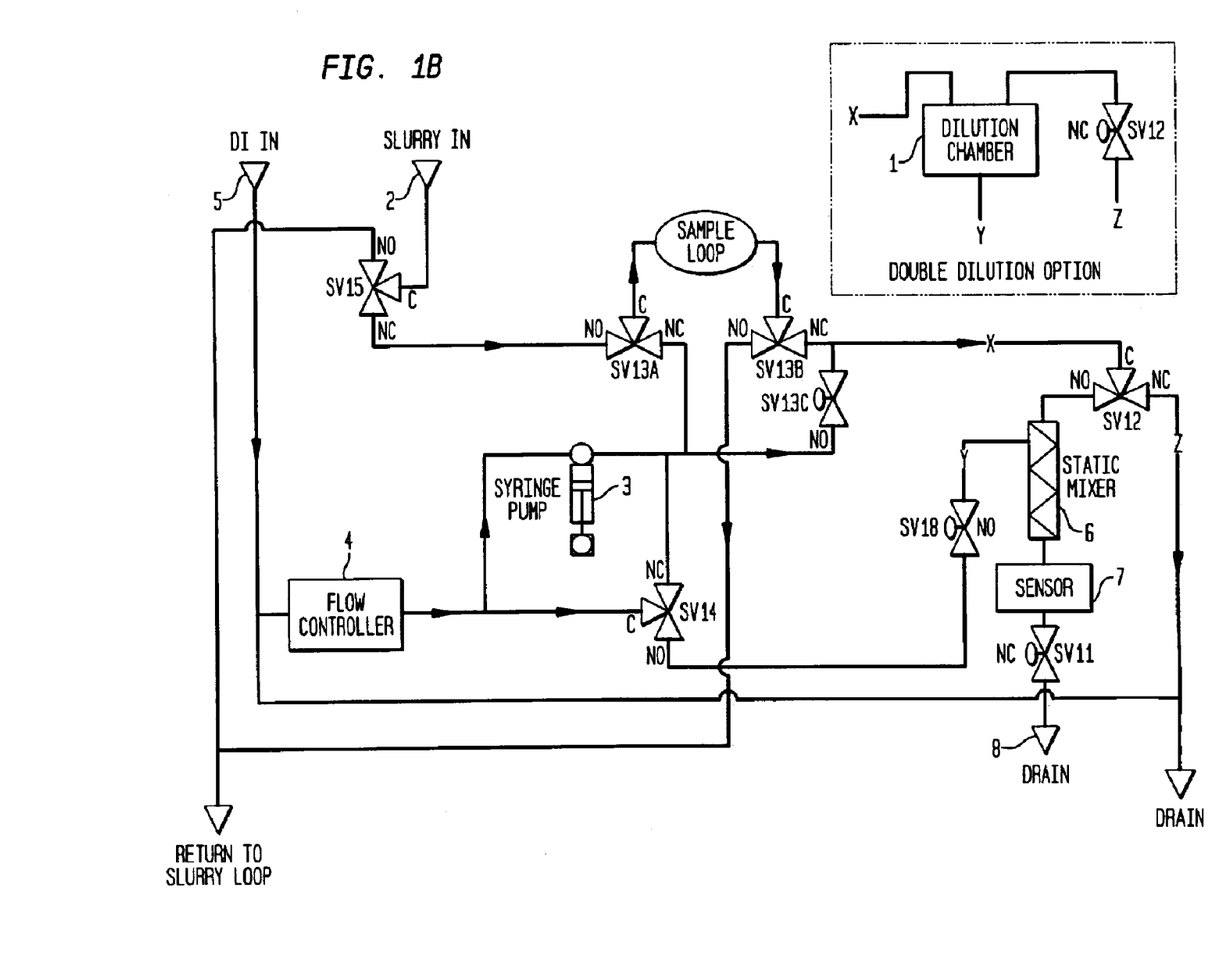
FIG. 1B is a schematic drawing of the AccuSizer system's auto-dilution apparatus.

The auto-dilution apparatus of the AccuSizer system and its operation are illustrated in and by FIGS. 1A and 1B. FIG. 1A is a table describing the ten operational steps of the AccuSizer system and the table contains typical times for each step, though the steps are not limited to these times. FIG. 1B is a schematic drawing of the system. The auto-dilution apparatus of the AccuSizer system is available in two formats, single dilution and double dilution. In the single dilution format, a slurry sample is captured in a sample loop, diluted in a mixer, and then the diluted sample is fed to a sensor for analysis. In the double dilution format, a slurry sample is captured in a sample loop, fed to a dilution chamber in which it is mixed with diluent to make a first diluted slurry, the first diluted slurry is then fed to the mixer in which it is mixed with additional diluent to make a second diluted slurry, and then this second slurry is fed to the sensor for analysis. The single dilution format is illustrated in FIG. 1B, and the double dilution format is also illustrated in FIG. 1B but with reference to the inset. The following description of the operation of the AccuSizer system is with respect to the double dilution format, yet the operation of the single dilution format is nearly the same but without reference to the dilution vessel (i.e., chamber).

The auto-dilution apparatus of the AccuSizer system operates in two stages. In the first stage (Steps 1–5), slurry sample is captured in a sample loop and diluted, and the sensor is prepared for slurry analysis. In the second stage (Steps 6–10), the slurry is analyzed and then flushed from the sensor.

The first stage starts with Step 1 of FIG. 1A, i.e., the simultaneous drawing of a fixed volume of sample (i.e., slurry) into the system and the flushing of dilution chamber 1 of FIG. 1B (i.e., the "vessel" in FIG. 1A). The function of Step 1 is two-fold, i.e., to capture sample for analysis and to ready the vessel to receive the sample.

During the sample loading sub-step of Step 1, valve SV15 is activated (i.e., opened) to capture a predetermined volume of slurry from slurry port 2, and syringe pump 3 is off. During the flushing of the dilution chamber (i.e., vessel flushing sub-step of Step 1), valves SV11 and SV12 are first opened, then valve SV11 is closed and valve SV14 is opened. Mass flow controller 4 is operational during the course of Step 1. Each sub-step of Step 1 takes about 30 seconds to complete but since these sub-steps occur simultaneously, the whole of Step 1 takes only about 30 seconds to complete.

In Step 2, mass flow controller 4 transfers deionized water (DI) into the system from DI port 5, through dilution chamber 1 and static mixer 6, and into sensor 7. During this operation, first valves SV11 and SV14 are opened, then SV12 and SV13 are opened; syringe pump 3 is initialized, and the mass flow controller is operational. Sensor 7 measures the background of the deionized water, which serves as the diluent for the slurry. Step 2 takes about 25 seconds to complete.

In Steps 3, 4 and 5, the slurry is diluted with the deionized and the diluted slurry is transferred to the sensor for analysis. The valve, syringe pump and the mass flow controller operations for these steps are described in FIG. 1A, and the time for each step is about 10, 40 and 0.5 seconds, respectively.

The second stage of the operation of the AccuSizer system's auto-dilution apparatus commences with Step 6, the actual analysis (i.e., the "measuring" of FIG. 1A) of the diluted slurry. This step takes about 60 seconds to complete and then in Steps 7–10, the diluted slurry is flushed from the system through exit port 8. The flush operations of Steps 8 and 9 are relatively long, e.g., about 90 seconds each, due to the need to insure that the sensor is rinsed clean of any residual slurry before the loading of another slurry sample into the system. The background check of Step 10 usually takes about 25 seconds to complete.

While the AccuSizer system's auto-dilution apparatus and others like it perform the basic task of diluting a slurry sample prior to its analysis by an OPC (or other sensor), it does so in a relatively inefficient manner. Each cycle of the AccuSizer system takes approximately 6 or more minutes to complete, but during this time data, e.g., PSD analysis of the diluted sample, is only collected for 60 seconds. The bottlenecks in this system are many, and they include sample capture, flush steps, background checks and the transfer of the sample to the dilution chamber by a syringe pump. Accordingly, the industry has a continuing interest in a dilution system that allows for more slurry analysis in less time with the concurrent elimination of one or more of the bottlenecks of the present systems. More generally, all industries have a continuing interest in performing efficient monitoring of the liquids used in their processes, and the elimination or moderation of any bottlenecks in these monitoring processes is always welcomed.

SUMMARY OF THE INVENTION

In one embodiment of this invention, a liquid sample dilution apparatus for producing a diluted liquid sample comprises:
  A. A first mixer manifold comprising:
    1. An inlet adapted to receive a diluent;
    2. A plurality of ports, each port adapted to receive a liquid sample;
    3. A mixing device for blending the liquid sample and the diluent to produce a first diluted liquid sample; and
    4. A first diluted liquid sample outlet; and
  B. Means for continuously delivering the diluent to the first mixer manifold inlet.

The means for continuously delivering the diluent includes, for example, a pressurized source and a flow controlling device, e.g., a pump, an orifice, a pipe constriction, etc.

In another embodiment, the dilution apparatus further comprises a second mixer manifold in fluid communication with the first mixer manifold and adapted to receive the diluted liquid sample from the first mixer manifold and to produce a second or further diluted liquid sample. The second mixer manifold can be of the same or different design as the first mixer manifold. For example, the second mixer manifold does not require one or more ports adapted to receive undiluted liquid sample.

The function and design of the sensor can vary to interest and in those embodiments in which particle size distribution is the property of interest, the sensor is typically an optical particle counter of any convenient design, e.g., a light scattering sensor, a light extinction sensor, a light scattering and light extinction combination sensor, etc. Each manifold mixer can be in fluid communication with the same sensor, or each manifold mixer can be in fluid communication with a different sensor.

In another embodiment, the invention is a method of continuously producing a diluted liquid sample for analysis by a sensor, the method comprising:
  Continuously introducing a diluent into a mixer manifold;
  Introducing a liquid sample into the mixer manifold;
  Mixing the diluent and liquid sample in the mixer manifold to produce a diluted liquid sample; and Transferring at least a portion of the diluted liquid sample to a sensor for analysis of at least one property of the diluted liquid sample.

In one variation on this embodiment, one portion of the diluted liquid sample is transferred to a first sensor and another portion of the diluted liquid sample is transferred to a second sensor.

In another embodiment, the invention is a method of continuously producing a diluted liquid sample for analysis by a sensor, the method comprising:

Continuously introducing a first diluent into a first mixer manifold;

Introducing a liquid sample into the first mixer manifold;

Mixing the diluent and first liquid sample in the first mixer manifold to produce a first diluted liquid sample;

Transferring at least a portion of the first diluted liquid sample to a second mixer manifold containing a second diluent;

Mixing the first diluted liquid sample with the second diluent to produce a second diluted liquid sample; and Transferring at least a portion of the second diluted liquid sample to a sensor for analysis of at least one property of the second diluted liquid sample.

While the diluent in these embodiments can be either aqueous or organic, typically the diluent is water, e.g., pH-adjusted, deionized or ultra-pure, and the liquid sample is an aqueous slurry, e.g., a chemical-mechanical polishing slurry. These methods can employ one or more sensors. The sensors can comprise any sensor that requires dilution and is capable of monitoring and/or analyzing the health of a liquid sample, e.g., the large particle tail of a CMP slurry. Suitable sensors are available from a host of different manufacturers, e.g., for CMP slurries the AccuSizer sensor from Particle Sizing Systems (PSS) of Santa Barbara, Calif., the HRLD 150 from Pacific Scientific, and the LiQuilaz-S05 from Particle Measuring Systems of Boulder, Colo. The flow rates of the first and second diluted liquid samples to the sensors can be the same or different. The dilution ratios for each sensor can be the same or different. The sensors can measure any one or more of a number of different properties including particle concentration, mean particle size distribution, zeta potential, and the like.

BRIEF DESCRIPTION OF THE DRAWINGS

Embodiments of the invention are disclosed with reference to the accompanying drawings and are for illustrative purposes only. The invention is not limited in its application to the details of CMP slurries, construction or the arrangement of the components, as illustrated in the drawings. The invention is capable of other embodiments or of being practiced or carried out in other various ways. Like reference numerals are used to indicate like components throughout the drawings. In the drawings, NO means "normally open", NC means "normally closed" and C means "common".

DETAILED DESCRIPTION OF THE PREFERRED EMBODIMENTS

Although the invention is described below in the context of slurries used in chemical-mechanical polishing processes, those skilled in the art will recognize that the invention can be employed with, and has applicability to, many other and different processes. "Liquid sample" and similar terms include slurries, colloids, emulsions, solutions, liquids containing gas, and the like, essentially any liquid comprising two or more components and that is amenable to dilution for purposes of analysis for one or more properties related to its composition.

Various items of equipment, such as fittings, valves, mountings, pipes, monitoring equipment, wiring, and the like have been omitted to simplify the description. However, such conventional equipment and its uses are known to those skilled in the art and can be employed as desired.

Figure 2:
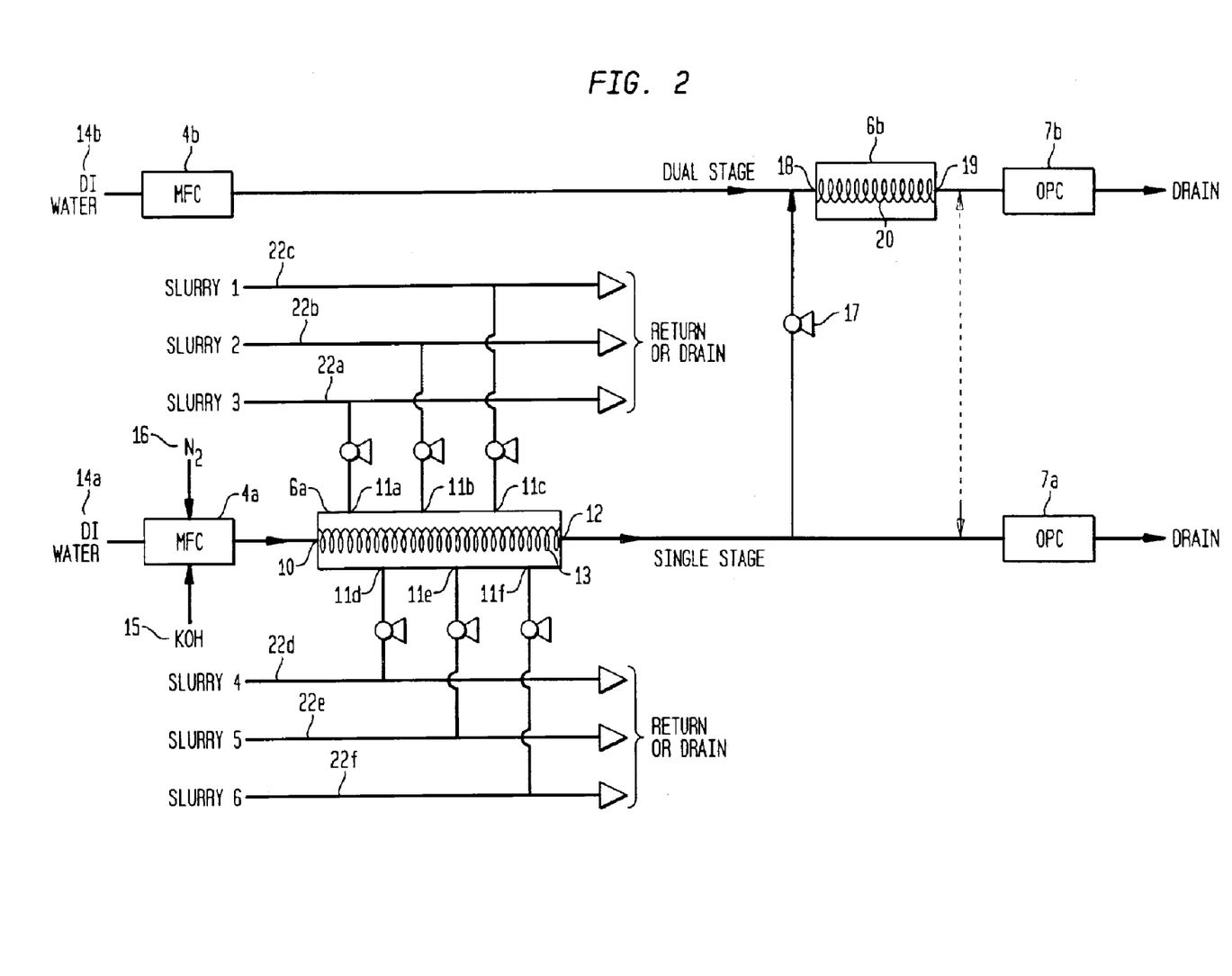
FIG. 2 is a schematic drawing of one embodiment of the dilution apparatus of this invention in combination with at least one sensor.

In FIG. 2, both a single-stage and dual-stage dilution apparatus are described. Both apparati comprise diluent-introducing means 4a and mixer manifold 6a. The dual stage apparatus also comprises diluent-introducing means 4b and mixer manifold 6b.

Mixer manifold 6a contains inlet 10, a plurality of slurry inlet ports 11a–f (collectively 11), outlet 12, and mixing element 13. Inlet 10 is adapted to receive the diluent (e.g., deionized water 14a), and is typically also adapted to receive a cleaning chemical (e.g., potassium hydroxide 15) and a purging fluid (e.g., nitrogen 16). Each slurry inlet port 11 is capable of receiving one of a plurality of slurries from one of a plurality of sample points within a CMP system (e.g., a "desired slurry"). The number of slurry inlet ports on the mixer can vary widely and to convenience. Outlet 12 is adapted to expel or otherwise discharge the diluted slurry, and is typically also adapted to expel the cleaning chemical, the purging fluid, and the diluent. Mixing element 13 can include one or more of a variety of devices structured to blend and/or mix one or more fluids and/or other substances together. For ease of design, construction and economic operation, static elements are preferred.

The diluent-introducing means, e.g., mass flow controller 4a, is employed to introduce the diluent into mixer manifold 6a at inlet 10. The diluent-introducing means (both 4a and 4b) of FIG. 2 is any means or device capable of delivering a constant flow (although not necessarily at a constant flow rate) to the mixers (both 6a and 6b) throughout the liquid sample monitoring operation. These means include pressurized sources of diluent, orifices, pipe constrictions, pumps, etc., with peristaltic pumps or preferred means. Diluent-introducing means 4a can and usually is used in combination with one or more pressure/flow regulators, pressure indicators, two-way valves, check valves, filters and flow restrictors (none of which are shown).

Slurry-introducing means (not shown) are employed to introduce a slurry into mixer manifold 6a at one of the plurality of ports 11. Slurry-introducing means can include one or more pumps or like devices capable of transporting a fluid through a conduit, pipe, or like structure. In a preferred embodiment, the slurry-introducing means comprises one or more bi-directional, peristaltic pumps. These pumps are capable of providing a broad range of slurry flow rates, and of carefully controlling a slurry flow rate during dilution of the slurry. These pumps are used to control the slurry flow rate so as to achieve an optimal dilution ratio of the slurry for measurement by a sensor. Each slurry will have an optimal dilution ratio. If multiple sensors are used, the optimal dilution ratio will likely be different for each sensor. The peristaltic pumps supply the desired slurry to mixer manifold 6a at ports 11. If more than one pump is used, then they are capable of operating simultaneously, sequentially, or individually, as desired.

Still referring to FIG. 2, the dual-stage embodiment of the dilution apparatus further includes, among other things, second mixer manifold 6b, second diluent-introducing means 4b, and an optional slurry-introducing means 17. Mixer manifold 6b contains inlet 18, outlet 19, and mixing element 20. Inlet 18 is adapted to receive the diluent and the diluted slurry, and it is typically also adapted to receive a cleaning chemical and a purging fluid. Outlet 19 is structured to expel or otherwise discharge the second diluted slurry, and is typically also adapted to expel the cleaning chemical, the purging fluid, and the diluent. Mixing element 20, like that of mixing element 13, can include a variety of devices structured to blend and/or mix one or more fluids and/or other substances together. Like mixer manifold 6a, diluent can also be introduced into mixer manifold 6b at inlet 18 by a diluent-introducing means.

Optional slurry-introducing means 17 is employed to introduce the diluted slurry from mixer 6a into mixer manifold 6b at inlet 18. Slurry-introducing means 17 can include a pump or like device capable of transporting a fluid through a conduit, pipe, or like structure. In a preferred embodiment, slurry-introducing means 17 comprises a bi-directional, peristaltic pump capable of supplying the diluted slurry to mixer manifold 6b at inlet 18. In another, less preferred embodiment, slurry-introducing means 17 is eliminated, and the diluted slurry is transferred from mixer 6a to mixer 6b simply by the pressure (or vacuum draw) available in the system.

The dilution apparatus is employed with one or more sensors 7a–b as shown in FIG. 2. Sensors 7a–b are capable of operating simultaneously, sequentially, or individually, as desired. In one embodiment, sensors 7a–b are connected to mixer manifolds 6a–b by one or more valves (not shown). By-pass of the sensors and removal or discharge from the sensors is accommodated by these valves. The discharge can be collected in one or more drains not shown.

In a preferred embodiment, operation of sensors 7a–b (i.e., performance of the sensors) can be monitored by comparing results that are generated by the sensors when each of the sensors measures the same diluted and/or further diluted slurry. Likewise, sensor 7a can measure a property of the diluted slurry, sensor 7b can measure a property of the second or further diluted slurry, and the properties of the first diluted slurry and the second diluted slurry can be compared.

Sensors 7a–b can, if desired, be produced by the same manufacturer and/or employ the same technique to measure slurry properties. However, sensors 7a–b can also be different from each other. For example, sensor 7a can use a light scattering technique to measure a property of a first diluted slurry and/or a second diluted slurry while sensor 7b can use a light extinction technique to measure a property of a first diluted and/or a second diluted slurry.

Each of sensors 7a–b are capable of on-line operation at least about ninety percent (90%) of the time that the dilution apparatus is operating. In an exemplary embodiment, each of sensors 7a–b are capable of continuous on-line operation. As here used, a sensor is considered to be on-line when the sensor is operating to measure a slurry property.

The dilution apparatus of this invention can also comprise a chemical introducing means (not shown). The chemical introducing means is selectively operable to introduce one or more cleaning chemicals into the dilution apparatus. The cleaning chemicals (e.g., potassium hydroxide 15, hydrochloric acid, etc.) can be employed to clean the dilution apparatus and/or remove unwanted slurry. The chemical introducing means can include one or more of, or combination of, a pressure/flow regulator, pressure indicator and valves.

The dilution apparatus can also comprise a purging fluid introducing means (not shown). The purging fluid introducing means is selectively operable to introduce one or more purging fluids (e.g., nitrogen 16) into the dilution apparatus. The purging fluids can be employed to clean the dilution apparatus and/or remove unwanted slurry, water, gases, and the like. The purging fluid introducing means can include one or more of, or combination of, a pressure/flow regulator, pressure indicator and check valves.

Diluent 14a from diluent-introducing means 4a flows through mixer manifold 6a almost continuously. In a preferred embodiment, diluent 14a flows through mixer manifold 6a prior to introduction of slurry into mixer manifold 6a. The slurry is then diluted as it is introduced into mixer manifold 6a, and the dilution system does not come into contact with concentrated slurry, which reduces the time required to flush the dilution system between cycles. The operation of mixer 6b relative to diluent 14b and diluent-introducing means 4b is essentially the same for the same reasons.

Figure 3:
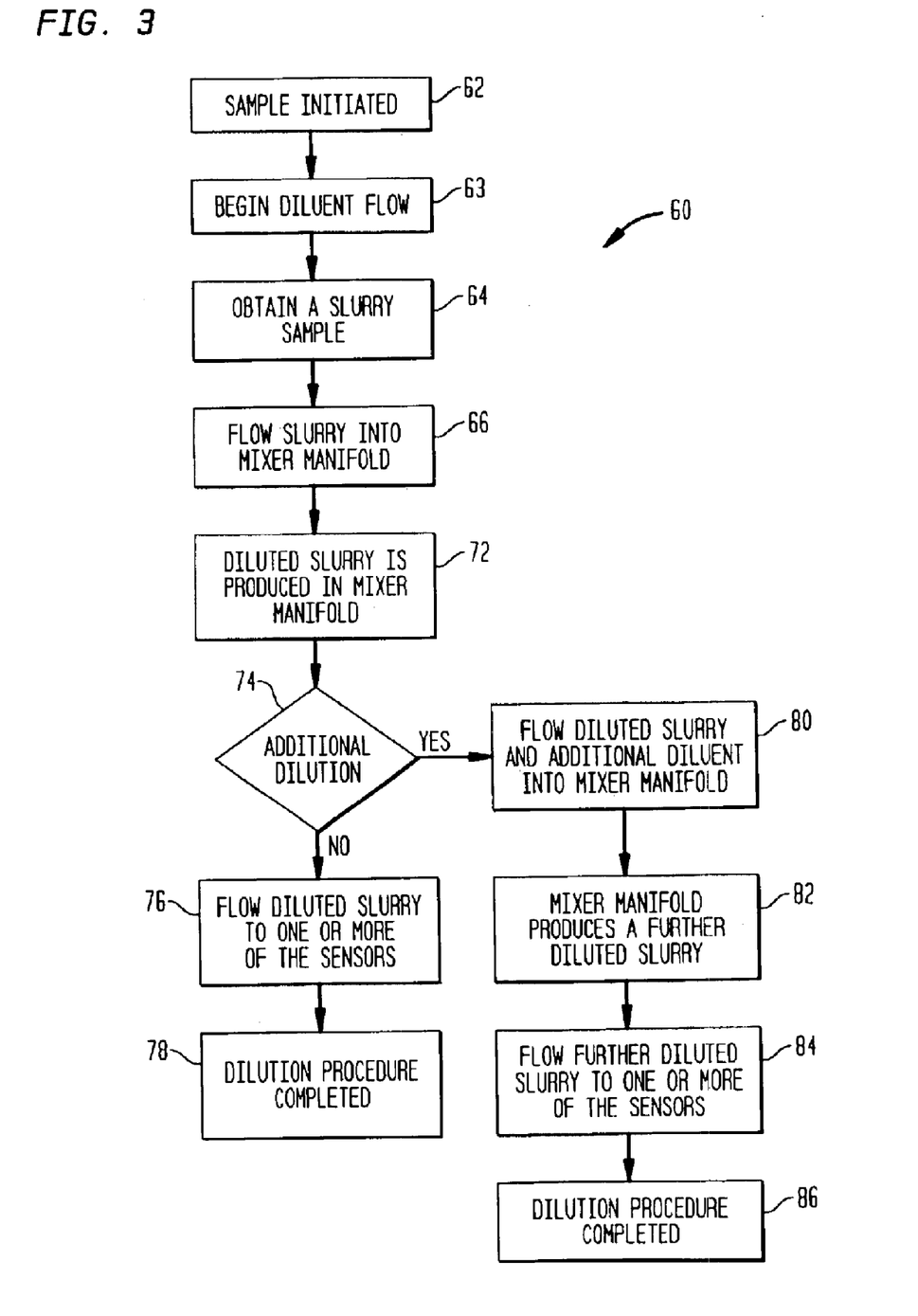
FIG. 3 is a flowchart outlining the steps for continuously producing a CMP diluted slurry using the dilution apparatus of FIG. 2.

In operation, as illustrated in FIG. 3, a procedure 60 for producing a first diluted slurry and a second diluted slurry using the dilution apparatus of FIG. 2 is outlined. When procedure 60 is initiated 62, the single stage of the dilution apparatus is employed such that diluent begins to flow 63 (or during continuous operation the diluent will already be continuously flowing) and one or more of a plurality of slurries from a plurality of sample points (i.e., a slurry sample) are obtained 64 by the slurry introducing means from one of the plurality of slurry lines 22a–f. The slurry is then introduced and/or flowed 66 into mixer manifold 6a by the slurry introducing means.

After receiving the slurry and the diluent, mixing element 13 within mixer manifold 6a mixes and/or blends 72 the slurry and the diluent such that a first diluted slurry is created, generated, and/or produced. Since the flow rate of the slurry and the diluent, relative to one another, entering mixer manifold 6a are known and can be manipulated, a first diluted slurry having a desired and/or optimum dilution ratio can be achieved.

Optionally, a determination 74 whether to further dilute the diluted slurry is made. If no further dilution is desired, the first diluted slurry can be provided and/or flowed 76 to one or both of sensors 7a–b such that one or more properties of the diluted slurry can be monitored. Thus, the dilution procedure is completed 78. If, however, further dilution is favored, the second stage is employed such that the first diluted slurry and additional diluent are introduced and/or flowed 80 into mixer manifold 6b by optional slurry-introducing means 17.

After receiving the first diluted slurry and the additional diluent, mixing device 20 within mixer manifold 6b mixes and/or blends the first diluted slurry and the additional diluent such that a second or further diluted slurry is created, generated, and/or produced. Since the flow rate of the first diluted slurry and the additional diluent, relative to one other, entering mixer manifold 6b are or can be known and can be manipulated, a second diluted slurry having a desired and/or optimum dilution ratio can be achieved.

The second diluted slurry can be provided and/or flowed 84 to one or both of sensors 7a–b such that one or more properties of the further diluted slurry can be monitored. Thus, the dilution procedure can once again be completed 86.

Diluent-introducing means 4a–b and each of the slurry-introducing means are capable of operating such that the diluent, the slurry, and the first diluted slurry are continuously introduced into mixer manifolds 6a–b. As a result, the dilution apparatus is capable of continuously producing the first and second diluted slurries. Thus, these diluted slurries can be continuously delivered to, and monitored by, sensors 7a–b.

The flow rate of the diluent into one or both of mixer manifolds 6a–b can be constant, fixed, and/or unchanging and a flow rate of the slurry and/or diluted slurry into one or both of mixer manifolds 6a–b can be adjustable, variable, and/or non-constant. Thus, the dilution apparatus of this invention, as noted above, can achieve the desired and/or optimum dilution ratios.

The dilution apparatus of this invention is believed to enhance and/or improve upon one or more qualities of a device such as the AccuSizer system if just the AccuSizer sensor is integrated into the dilution apparatus of this invention. The dilution system of this invention can have diluent constantly coursing through it and as such, the slurry sample is injected directly into the diluent. This means that the dilution system of this invention sees little if any concentrated slurry and this, in turn, makes flushing of the system fast and easy. Furthermore, over a six minute cycle, the dilution system of this invention can collect as much as five or more minutes of data whereas the AccuSizer system typically collects 1 minute of data in a six minute cycle. If measurement of only one slurry is desirable, the sensor and dilution apparatus of this invention could measure slurry continuously (for several weeks) except during times of periodic maintenance.

Obtaining data as often as possible is desirable for several reasons. One reason is so that any problems with the slurry can be rapidly detected. Slurry must travel through pumps, valves, tubing, filters, etc. before it arrives at a polisher. The slurry is typically circulated through these components in order to prevent settling and/or stagnation. In this arrangement, the polishers are located on slipstreams off of the main slurry loop and the polishers demand slurry only when they require it. However, as the slurry is subjected to multiple passes in the loop, the slurry "health," in particular the slurry PSD, may detrimentally change. Slurry PSD can change for a variety of reasons such as a failed component like a valve or filter, agglomeration of the slurry particles resulting from recirculation, adding a new tote of slurry with a higher concentration of particles or a water leak into the slurry loop. Therefore, monitoring the slurry PSD as frequently as possible, ensures that slurry problems can be detected quickly and immediate action taken to remedy the problem.

Another reason for increasing the measurement frequency is to improve the variability of the slurry health parameter measurements. The results of measurements, in which events that occur at random are counted at a definite average rate, can be described by the Poisson distribution. If one counts the occurrences of this type over time and obtains, on average, $\overline{N}$ counts, then the uncertainty in the measurement as expressed by the standard deviation is $\pm\sqrt{\overline{N}}$. This is sometimes referred to as the "square-root rule." The standard deviation ($\sigma$) of the AccuSizer data, assuming the concentration is invariant, can be approximated by the square-root rule. In the case of the AccuSizer, $\overline{N}$ equals the average number of particles counted at a given particle diameter for individual measurements of equal length. The variability (at $3\sigma$) of the AccuSizer data can be calculated as shown in Equation 1. The percent relative standard deviation (% RSTD) can be calculated as shown in Equation 2.

$$\text{Variability }(3\sigma) = 3 \times \text{StandardDeviation} = 3\sigma = 3 \times \sqrt{\overline{N}} \qquad (1)$$

$$\% \text{ Relative Standard Deviation} = \frac{3 \times \sqrt{\overline{N}}}{\overline{N}} \times 100\% = \pm \frac{3 \times 100\%}{\sqrt{\overline{N}}} \qquad (2)$$

The abilities of sensors, and systems with sensors integrated into a dilution apparatus, to detect changes in slurry properties can be compared using the % RSTD of particle counts measured by each sensor or system. Equation 2 indicates that as the number of particles counted increases, the % RSTD decreases. Since the % RSTD is a measurement of the "noise," ideally the % RSTD should be as low as possible so small changes in the slurry PSD can be detected. Increasing the duration of the PSD measurement, results in more particles being counted, which leads to a lower % RSTD, thus lower measurement variability.

To demonstrate certain benefits of the dilution system of this invention, an AccuSizer system was directly compared to a test system in which an AccuSizer sensor was integrated into the dilution system of this invention. As here used, "test system" refers to the combination of the AccuSizer sensor and the dilution system of this invention.

Figure 4:
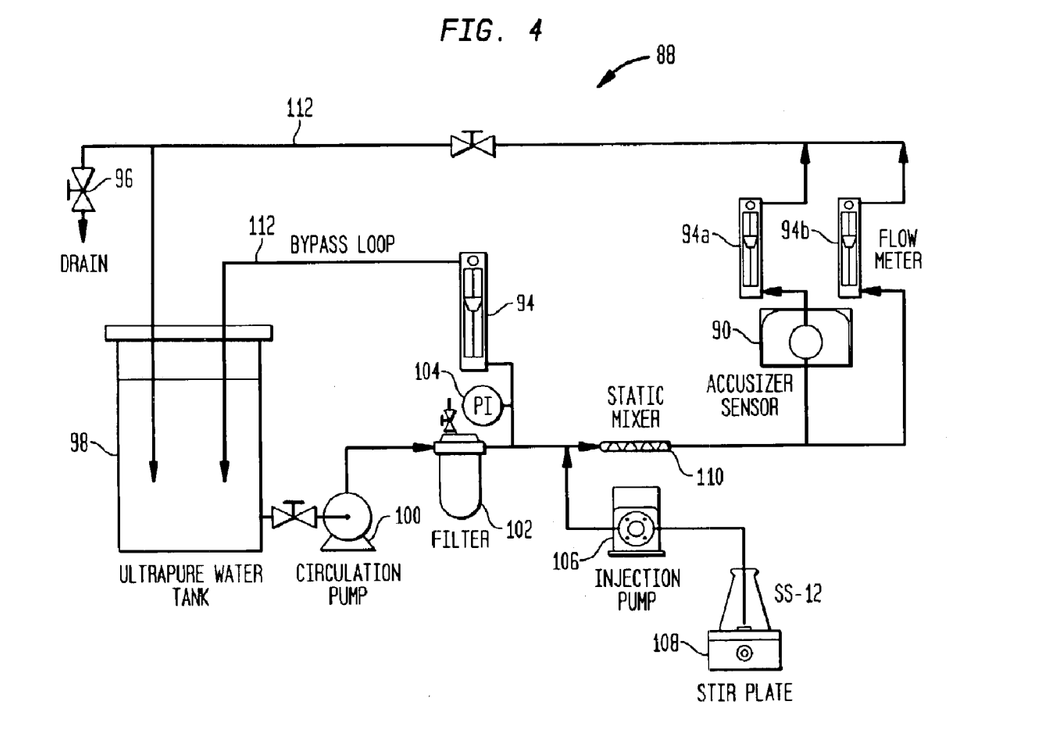
FIG. 4 is a schematic representation of a test system constructed to compare a first sensor and a second sensor when the dilution apparatus of FIG. 2 is used.

The test system is shown in FIG. 4. System 88 generally comprised, among other things, AccuSizer sensor 90, flow meters 94a–b, drain 96, tank 98, circulation pump 100, filter 102, pressure gauge 104, injection pump 106, stir plate 108, static mixer 110, and lines 112.

Test system 88 produced diluted slurry comparably and/or similarly to the dilution apparatus of this invention and, therefore, allowed the AccuSizer system to be compared with the test system. Repeated measurements of Cabot SS-12 slurry were taken with the AccuSizer system and the test system in order to determine the % RSTD of data collected by each system. The same sensor and same lot of Cabot SS-12 slurry were used in both systems, so the only difference between the two systems was the dilution system. The Table summarizes the results obtained from this comparison. The % RSTD for various particle diameters is provided for each system. Notably, the variability of the AccuSizer system was about 4 times larger than the variability of the test system for each of the particle diameters shown. This suggests that the test system can detect smaller changes, approximately one-quarter of the magnitude, than the AccuSizer system.

TABLE

Comparison of the AccuSizer System with the Test System

| Particle Diameter | Variability (% RSTD @ 3σ) | |
|---|---|---|
| (μm) | AccuSizer system | Test system |
| ≧0.5 | 12.4% | 3.4% |
| ≧1.0 | 28.5% | 8.2% |
| ≧2.0 | 42.0% | 12.0% |
| ≧5.0 | 47.0% | 13.5% |
| ≧10.0 | 60.0% | 15.6% |

As test system 88 and the Table confirm, qualities of the AccuSizer sensor were enhanced and/or improved when a dilution apparatus capable of continuously producing diluted slurry, such as the dilution apparatus of this invention, was used in lieu of the auto-dilution apparatus found within the AccuSizer system. Simply put, the test system that included the AccuSizer sensor component was more repeatable and more efficient than the AccuSizer system, thereby allowing smaller changes in slurry health parameters, particularly changes in the large particle tail, to be detected.

Despite any methods being outlined in a step-by-step sequence, the completion of acts or steps in a particular chronological order is not mandatory. Further, elimination, modification, rearrangement, combination, re-ordering, or the like, of acts or steps is contemplated and considered within the scope of the description and appended claims. Also, while the present invention has been described in terms of the preferred embodiment, equivalents, alternatives and modifications, aside from those expressly stated, are possible and within the scope of the description and appended claims. All U.S. patents and allowed U.S. patent applications cited in this specification are incorporated herein by reference.

What is claimed is:

1. A liquid sample dilution apparatus for producing a diluted liquid sample, the liquid sample dilution apparatus comprising:
   (a) a first mixer manifold comprising:
      an inlet adapted to receive a diluent;
      a plurality of ports, each port adapted to receive a distinct liquid sample;
      a mixing device for blending the liquid sample and the diluent to produce a first diluted liquid sample; and
      a first diluted liquid sample outlet; and
   (b) means for continuously delivering the diluent to the first mixer manifold inlet.

2. The apparatus of claim 1 further comprising means for delivering the liquid sample to a first mixer manifold port.

3. The apparatus of claim 2 in which the means for delivering the liquid sample to a first mixer manifold port is a flow controlling device.

4. The apparatus of claim 3 in which the flow controlling device is a pump.

5. The apparatus of claim 1 in which the means for continuously delivering the diluent to the first mixer manifold inlet is a flow controlling device.

6. The apparatus of claim 1 in fluid communication with a sensor, the sensor adapted to receive and analyze at least one property of at least a portion of the first diluted liquid sample.

7. The apparatus of claim 6 in which the sensor is an optical particle counter.

8. The apparatus of claim 1 further comprising a second mixer manifold in fluid communication with the first mixer manifold such that the second mixer manifold receives at least a portion of the first diluted liquid sample from the first mixer manifold, the second mixer manifold comprising:
   (a) a diluent inlet;
   (b) a first diluted liquid sample inlet;
   (c) a mixing device for blending the first diluted liquid sample and the diluent to produce a second diluted liquid sample; and
   (d) a second diluted liquid sample outlet.

9. The apparatus of claim 8 further comprising means for continuously delivering diluent to the second mixer manifold diluent inlet.

10. The apparatus of claim 9 in which the second mixer manifold is in fluid communication with a sensor such that the sensor receives at least a portion of the second diluted liquid sample, the sensor adapted to analyze at least one property of the second diluted liquid sample.

11. The apparatus of claim 10 in which the sensor is an optical particle counter.

12. The apparatus of claim 9 in which both the first and second mixer manifolds are in fluid communication with a sensor adapted to receive and analyze at least one property of the first and second diluted liquid samples.

13. The apparatus of claim 12 in which the first and second mixer manifolds are in fluid communication with the same sensor.

14. The apparatus of claim 12 in which the first and second mixer manifolds are in fluid communication with different sensors.

15. The apparatus of claim 13 in which the sensor is an optical particle counter.

16. The apparatus of claim 14 in which the sensors are optical particle counters.

17. A method of continuously producing a diluted liquid sample for analysis by a sensor, the method comprising:
   continuously introducing a diluent into a mixer manifold;
   introducing one of a plurality of liquid samples into one of a plurality of liquid sample ports in the mixer manifold wherein each port is adapted to receive a distinct liquid sample;
   mixing the diluent and liquid sample in the mixer manifold to produce a diluted liquid sample; and
   transferring at least a portion of the diluted liquid sample to a sensor for analysis of at least one property of the diluted liquid sample.

18. The method of claim 17 in which one portion of the diluted liquid sample is transferred to a first sensor and another portion of the diluted liquid sample is transferred to a second sensor.

19. The method of claim 17 in which the diluent is water, and the liquid sample is a slurry.

20. The method of claim 19 in which the liquid sample is a chemical-mechanical polishing slurry and is analyzed for particle size distribution.

21. A method of continuously producing a diluted liquid sample for analysis by a sensor, the method comprising:
   continuously introducing a first diluent into a first mixer manifold;
   introducing a liquid sample into the first mixer manifold;
   mixing the diluent and first liquid sample in the first mixer manifold to produce a first diluted liquid sample;
   introducing a second diluent into a second mixer manifold;
   transferring at least a portion of the first diluted liquid sample to the second mixer manifold;
   mixing the first diluted liquid sample with the second diluent to produce a second diluted liquid sample; and
   transferring at least a portion of the second diluted liquid sample to a sensor for analysis of at least one property of the second diluted liquid sample.

22. The method of claim 21 further comprising transferring at least a portion of the first diluted liquid sample to a sensor for analysis of at least one property of the first diluted liquid sample.

23. The method of claim 22 in which the first and second diluted liquid samples are transferred to the same sensor.

24. The method of claim 22 in which the first and second diluted liquid samples are transferred to different sensors.

25. The method of claim 21 in which the first and second diluents are water, and the liquid sample is a slurry.

26. The method of claim 25 in which the liquid sample is a chemical-mechanical polishing slurry and is analyzed for particle size distribution.

27. A system for continuously diluting a liquid sample during analysis by a sensor comprising:

a mixer manifold comprising: a mixing element, a diluent inlet, a plurality of liquid sample ports each in fluid communication with one of a plurality of liquid sample points, and an outlet;

means for continuously delivering diluent to the diluent inlet; and a sensor in fluid communication with the outlet.

28. The system of claim 27 further comprising means for continuously delivering a liquid sample to one of the plurality of liquid sample ports.

29. The apparatus of claim 28 in which the means for delivering the liquid sample to the liquid sample port is a flow controlling device.

30. The apparatus of claim 29 in which the flow controlling device is a pump.

* * * * *